(12) United States Patent
Yang

(10) Patent No.: US 8,642,532 B2
(45) Date of Patent: Feb. 4, 2014

(54) EXCIPIENTS FOR PROTEIN STABILIZATION

(76) Inventor: Guohan Yang, Mansfield, MA (US)

( * ) Notice: Subject to any disclaimer, the term of this patent is extended or adjusted under 35 U.S.C. 154(b) by 508 days.

(21) Appl. No.: 12/739,402

(22) PCT Filed: Nov. 17, 2008

(86) PCT No.: PCT/US2008/083793
§ 371 (c)(1),
(2), (4) Date: Aug. 27, 2010

(87) PCT Pub. No.: WO2009/065126
PCT Pub. Date: May 22, 2009

(65) Prior Publication Data
US 2011/0046052 A1 Feb. 24, 2011

Related U.S. Application Data

(60) Provisional application No. 60/988,494, filed on Nov. 16, 2007.

(51) Int. Cl.
*A61K 38/00* (2006.01)
*A01N 37/10* (2006.01)
*C07C 309/00* (2006.01)

(52) U.S. Cl.
USPC ............ 514/1.1; 514/532; 514/543; 514/544; 562/45

(58) Field of Classification Search
None
See application file for complete search history.

(56) References Cited

U.S. PATENT DOCUMENTS

| 6,211,144 B1 | 4/2001 | Havelund |
| 6,489,292 B1 | 12/2002 | Havelund et al. |
| 6,652,885 B2 | 11/2003 | Steiner et al. |
| 6,890,518 B2 | 5/2005 | Patton et al. |
| 6,960,561 B2 | 11/2005 | Boderke |
| 7,021,309 B2 | 4/2006 | Gonda et al. |
| 7,490,603 B2 | 2/2009 | Gonda et al. |
| 7,648,960 B2 | 1/2010 | Steiner et al. |
| 2003/0125234 A1 | 7/2003 | Middaugh |

FOREIGN PATENT DOCUMENTS

| WO | WO-2006/042848 A2 | 4/2006 |
| WO | WO-2006/042848 A3 | 4/2006 |

OTHER PUBLICATIONS

Kornecki et al.: Am J Physiol Heart Circ Physiol 238:H54-H60, 1980.*
STN results returned on May 22, 2013; pdf attached.*
Ben-Zvi, A. et al. (Sep. 3, 2004). "Active Solubilzation and Refolding of Stable Protein Aggregates by Cooperative Unfolding Action of individual Hsp70 Chaperones," *The Journal of Biological Chemistry* 279(36):37298-37303.
Chang, B.S. et al. (2002). "Paractical Approaches to Protein Formulation Development," Chapter 1 in *Ratrional Design of Stable Protein Fourulations: Theory and Practice*, Carpenter, J.F. ed. et al., Kluwer Academic/Plenum Publishers, New York, NY, pp. 1-25.
Dayhoff, M.O. et al. (Sep. 1978). "A Model of Evolutionary Change in Proteins," Chapter 22 in *Atlas of Protein Sequence and Structure*. The National Biomedical Reseach Foundation: Silver Spring, MD, pp. 345-352.
Gestwicki, J.E. et al. (Oct. 29, 2004). "Harnessing Chaperones to Generate Small-Molecule Inhibitors of Amyloid β Aggregation," *Science* 306(5697):865-869.
International Search Report mailed Jun. 22, 2009 for PCT Application No. PCT/US2008/083793, filed Nov. 17, 2008, two pages.
Pearlman, R. et al. eds. (1996). *Formulation, Characterization, and Stability of Protein Drugs: Case Histories*, Plenum Press, New York, NY, pp. xix-xxviii. (Table of Contents Only.)
Written Opinion mailed o Jun. 22, 2009, for PCT Application No. PCT/US2008/083793, filed on Nov. 17, 2008, three pages.

* cited by examiner

*Primary Examiner* — Robert A Wax
*Assistant Examiner* — Jeffrey T Palenik
(74) *Attorney, Agent, or Firm* — Helen S. Liu

(57) ABSTRACT

This invention is a method of using a class of excipients for protein formulation to reduce and/or eliminate protein aggregation in solutions or solids. This class of compounds contains carbonyl group(s) to form Schiff base(s) with amino groups of proteins and also contains moieties to keep protein molecules spatially separated. This method has never been disclosed anywhere in the literature.

6 Claims, 7 Drawing Sheets

EXCIPIENTS FOR PROTEIN STABILIZATION

CROSS-REFERENCE TO RELATED APPLICATIONS

This application claims the benefits of PCT/US08/08379 filed November 2008, which is incorporated by reference in its entirety herein.

BACKGROUND

With the well-developed DNA recombinant technology, more and more proteins are being developed as pharmaceuticals. Development of stable protein formulations is one of the critical steps in developing protein as a therapeutic product. A vast amount of research has been conducted regarding protein stability, and this information is readily available in the literature. (a. Pearlman, R. and Wang, Y. J., 1996. Formulation, characterization, and stability of protein drugs. Plenum Press, New York. B. Chang, B. S. and Hershenson S., Chapter 1, Practical Approaches to Protein Formulation Development, Rational Design of Stable Protein Formulations, edited by Carpenter and Manning Kluwer Academic & Plenum Publishers, New York, 2002) However, due to the very nature of proteins, it is not practical for most of proteins to have only the native form of a protein in the formulation. More or less, proteins are formulated into solutions or solids (lyophilized, spray-dried, spray-freeze-dried) together with excipients to maximize protein stability during manufacturing process and during storage.

Besides various chemical reactions, such as disulfide scrambling, deamidation, peptide cleavage, oxidation, a major instability problem relates to non-covalent aggregation that is often immunogenic and sometimes produces precipitates. In liquid formulation, optimization of pH, ionic additives, aminoacid, surfactants, protein concentration and raw material purity may provide solutions to the aggregation problem. In solid formulation, proteins are usually formulated together with some buffer reagents, salt, and some bulky reagents such as mannitol, sucrose, trehalose, citric acid etc. to physically separate protein molecules, and thus to reduce aggregate formation.

Chaperones can also reportedly reduce or prevent aggregation. (Anat Ben-Zvi, Paolo De Los Rios, Giovanni Dietler, Pierre Goloubinoff, Active Solubilization and Refolding of Stable Protei Aggregates By Cooperative Unfolding Action of Individual Hsp70 Chaperones, The Journal of Biological Chemistry, Vol. 279, No. 36, Issue of September 3, 37298-37303, 2004). It is also reported that a Congo Red conjugate which binds to both FK506 binding protein and beta-amyloid peptide hinders the amyloid fibrillation. (Science, 306, 865, 2004)

In case of insulin, there are many methods to minimize insulin fibrillation that leads to aggregate precipitation from solution. Addition of zinc induces insulin to form a hexamer complex which contains two zinc per six insulins, and this complex is much more stable than monomeric insulin. Phenol, m-cresol are also used to improve insulin stability, Svend Havelund of Novo Nordisk tried to improve stability of liquid insulin for pulmonary delivery by optimizing the additive ratios, achieving marginal improvement. (U.S. Pat. Nos. 6,211,144, and 6,489,292) Peter Boderke of Aventis Pharama used zinc, Tween-20, Tween-80, Poloxamer 171 to achieve insulin stability 5-7 folds longer before fibrils precipitate (U.S. Pat. No. 6,960,561 B2)

Monomeric insulin has found its application in formulations for pulmonary delivery where it showed its superiority over hexameric zinc insulin. Solomon Steiner et al of Mannkind Corporation formulated zinc free insulin into microspheres with a diketopiperazine bulk reagent (U.S. Pat. No. 6,652,885 B2) for inhalation, and Igor Conda et al of Aradigm corporation formulated insulin lispro into solution for nebulized inhalation. Those monomeric insulins showed their advantage primarily due to their superior solubility and faster absorption through lung membrane.

Chemical modification using polyethylene glycol is also used to improve protein stability. However, it changes the protein chemically, and often decreases the biological activity of the protein.

SUMMARY OF THE INVENTION

This invention relates to the application of a class of excipients in the formulation of proteins, including therapeutic proteins, in the form of solutions, gels and solids with an intention to minimize and eliminate protein aggregation. This invention is also related to application of a class of excipients in the manufacturing process in which this class of excipients stabilize proteins. This invention also relates to application of this class of excipients in protein formulations for bulk storage. This present invention also relates to improving on-shelf storage stability of protein products including therapeutic proteins. This invention also relates to improving solubility of proteins and to improving easiness of reconstitution of solid protein products. This invention also relates to their application in protein formulations in combination with saccharide excipients like sucrose, and relates to their application to replace saccharide excipients to reduce solution viscosity when at high concentration.

A new formulation method to minimize protein aggregation using a class of chemical compounds bearing carbonyl group(s) and charges or bulky group(s). The carbonyl group(s) are to form reversible Schiff bond formation with amino groups of protein surface, while the charges and/or bulky group(s) are to change protein surface characteristics.

A class of chemical compounds bearing the following structural features as excipients for protein formulations. In addition to this structural example, other structural arrangements can also provide the desired structural features to be suitable excipients, as long as they carry one or more carbonyl groups to form Schiff base with proteins, and also carry positive and/or negative charges and/or bulky substituents.

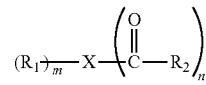

Where:

$R_1$ or $R_2$ carries desired positive and/or negative charges at formulation pH preferably near physiological pH, or around the pH the formulated product has the optimized stability. "m" is 1, or 2, or 3, or 4, or 5.

Or $R_1$ or $R_2$ carries a bulky chemical moiety including saccharides, polyethylene glycols, peptides, nucleic acids, polyhydroxy moiety that does not undergo Maillard reaction.

$R_2$ is hydrogen or an alkyl or aromatic group. "n" is 1, or 2, or 3.

$R_1$ or $R_2$ carries one or more carbonyl groups to further dynamically stabilize Schiff base formation.

X is a chemical moiety connecting $R_1$ and $R_2$. X can be a carbon-containing linear chain, or a ring or an aromatic ring, or a simple chemical bond.

Application of the class of chemical compounds bearing the chemical features listed above, in protein manufacturing process, or in protein formulation with an intention to deter or prevent proteins of interest from forming aggregates that can be soluble or insoluble.

A protein formulation method using the chemicals above in the forms of solution, solids prepared from various methods including but not limited to crystallization, precipitation (induced by temperature change or addition of benign organic solvent), spray dry, spray-freeze dry, lyophilization.

A protein formulation method using the chemicals above individually, or in their combinations, or their combinations with other appropriate excipients.

A protein formulation method using the chemicals above, for the purpose of protection and/or prolonged on-shelf life span of therapeutic protein reagents.

Application of this class of excipients in a process of protein purification and manufacturing.

Application of his class of excipients into a protein formulation for bulk storage.

Application of this class of excipients to replace saccharide excipients such as sucrose, trehalose etc. in a protein formulation in order to reduce viscosity and/or foaming of a protein solution and/or of a reconstituted solution.

A stabilized protein formulation using excipients above, for prolonged storage under refrigerated and/or non-refrigerated conditions, and/or for the ease of re-constitution protein reagents.

A stabilized protein formulation using excipients above, for the purpose of increasing protein solubility, and/or for the ease of re-constitution of a solid formulation prior to drug administration.

A stabilized formulation of zinc insulin or zinc-free insulin, insulin analogs such as LisPro and Insulin Aspartate with or without zinc, using excipients above, in forms of liquid and solid, for the drug delivery purpose by means of nasal spray, or pulmonary and/or nebulized inhalation, or injection using methods including but not limited to syringes, pens and pumps.

A stabilized insulin liquid formulation using excipients above, for prolonged storage under refrigerated and/or non-refrigerated conditions.

A stabilized insulin solid formulation using excipients above, for prolonged storage under refrigerated and/or non-refrigerated conditions and for the ease of re-constitution before drug administration.

DETAILED DESCRIPTION OF THE INVENTION

Figure 1:
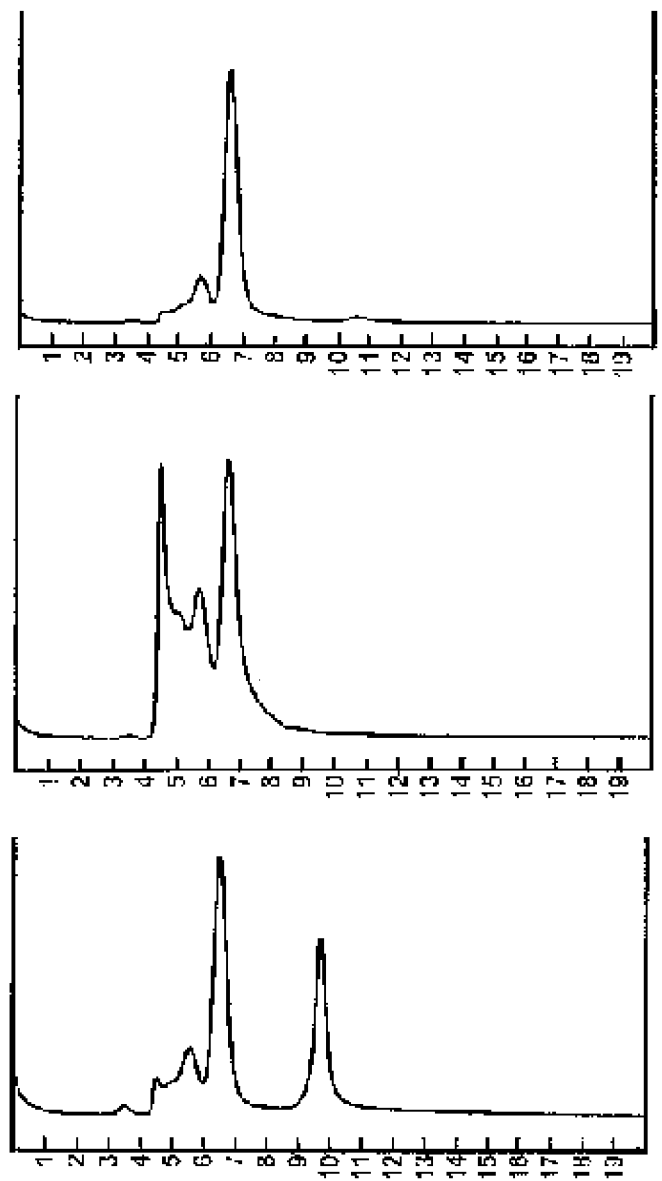
FIG. 1 SEC HPLC profiles of BSA Methanol-Induced Aggregation Inhibited by Pyridoxal Phosphate (X2);
Top: Commercial BSA as reference (Sigma Aldrich),
Middle: BSA after treatment with methanol,
Bottom: BSA after treatment with methanol in the presence of excipient X2, FIG. 2 SEC HPLC profiles of Incubated BSA With and Without 5-Formylbenzene-1,3-disulfonic Acid (X5); Top first, fresh BSA reference, Heated samples: [BSA]=262 mg/ml, 50 mM sodium phosphate, pH 7.4, 65° C., 60 minutes, with excipient,
[X5]=12.5 mg/ml (top second),
[X5]=25.0 mg/ml (top third),
[X5]=50.0 mg/ml (bottom).

Proteins form aggregates primarily due to surface interaction of hydrophobic regions. Many excipients, such as saccharides and aminoacids, are used in protein formulations, and they are intended to "coat" protein surface through hydrogen bonding, and to form a barrier to separate protein molecules. In this way, protein aggregation can be reduced. It is also common to optimize pH to change the protein surface charge characteristics to affect protein aggregation process. Proteins and many peptides have significant number of lysine residues in their sequences, and lysine carries an amino group on its side chain. At physiological pH and below, this lysine side chain is mostly protonated and carries a positive charge, and so does the N-terminal amine This invention is to take advantage of the presence of lysine and N-terminal amine in the protein sequences, to change its surface characteristics using a class of excipients that have never been used in protein formulations. Those excipients are generally regarded as safe, based on the common knowledge in the field of chemistry and pharmaceuticals formulation.

The first approach is to convert lysine side chain to carry one or more charges, preferably negative charges. This alters the surface charge characteristics of a protein to increase the repulsive force between protein molecules, to increase protein solubility, and to reduce surface hydrophobicity. In order to achieve this surface charge modification while maintaining chemical integrity of the protein molecule, a reversible Schiff base formation is chosen to facilitate the binding of excipients to protein surface. If the excipient molecule carries one or more charges, preferably negative charges, and the excipient is set at an optimized concentration, the protein surface is effectively changed. The negative charges can be from carboxylic acids, sulfonic acids, sulfenic acids, sulfates, phosphoric acids, phosphates, peptides, nucleic acids, carboxymethyl cellulose, carboxyethyl cellulose and so on. Chitosan, polyethyleneimine, peptides containing histidine and arginine, and some surfactants can serve as providers of positive charges. A few examples are listed below to illustrate the chemical structural characteristics of this class of excipients, while useful excipient candidates are not limited to these examples.

Scheme 1 Examples of Relevant Excipient Candidates

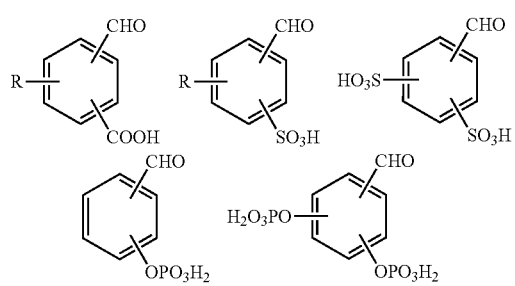

-continued

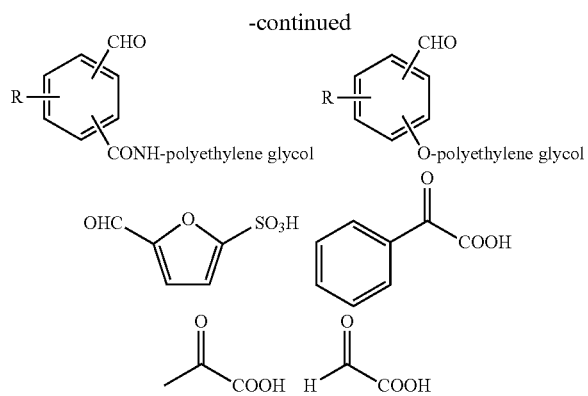

The chemical excipients of the invention include 2-formylbenzene sulfonic acid, pyridoxal phosphate, 4-formylbenzene-1,3-disulfate, 4-formylbenzoic acid, 3-formyl-4-hydroxyl-benzoic acid, 4-formyl-3-hydroxyl-benzoic acid, phenylglyoxylic acid, glyoxylic acid, and pyruvic acid.

The second approach is to convert lysine side chain to carry a water-soluble benign bulky molecule, to physically block protein-protein interactions. In order to achieve this surface modification without chemically changing the protein molecules, a reversible Schiff base formation is chosen to facilitate the binding of excipients to protein surface, while excipient molecules carry a bulky side chain, such as polyethylene glycol, saccharides, oligosaccharides, polysaccharides, peptides, nucleic acids, chitin, chitosan, carboxymethyl cellulose, carboxyethyl cellulose and so on.

The excipients of this invention have chemical structural features below as an example. In addition to this structural example, other structural arrangements can also provide the desired structural features to be a suitable excipients, as long as they carry one or more carbonyl groups to form Schiff base with proteins, and a positive and/or negative charges and/or bulky substituents.

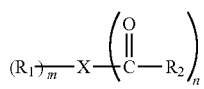

Where:

$R_1$ carries desired positive and/or negative charges at formulation pH, preferably near physiological pH, or around the pH the fore formulated product has the optimized stability. "m" is 1, or 2, or 3, or 4, or 5.

Or $R_1$ carries a bulky chemical moiety including saccharides, polyethylene glycols, peptides, nucleic acids, polyhydroxy moiety that does not undergo Maillard reaction.

$R_2$ is hydrogen or an alkyl or aromatic group. "n" is 1, or 2, or 3.

$R_1$ or $R_2$ carries one carbonyl group or more carbonyl groups to further dynamically stabilize Schiff base formation.

X is a chemical moiety connecting $R_1$ and $R_2$. X can be a carbon-containing linear chain, or a ring or an aromatic ring, or a simple chemical bond.

Example 1

Inhibition of Thermal Aggregation of Bovine Serum Albumin (BSA)

A 0.050 ml of BSA stock solution (35%, in water, 0.85% sodium chloride, from Sigma) was diluted into 0.450 ml of sodium phosphate buffer (50 mM, pH 7.4, 0.85% sodium chloride) to give a BSA solution at concentration of 35 mg/ml. An excipient, 2-formylbenzenesulfonic acid, sodium salt (Aldrich, 75%), was made into a solution in water (HPLC grade) at concentration of 75 mg/ml, and its pH was adjusted to 8 using dilute hydrochloric acid.

An aliquot of 0.050 ml of the above stock BSA solution (35 mg/ml) was diluted into PBS buffer (pH 7.4, 0.80 ml), and 0.15 ml of the excipient solution was added to it to make a BSA concentration of 1.75 mg/ml, and the excipient of 11.25 mg/ml. A separate sample was prepared without the addition of the excipient. Both samples in capped glass tubes are incubated at 65° C. At intervals of 0, 40 minutes, aliquots are withdrawn for HPLC analysis on size exclusion chromatography (SEC) column, eluted with PBS buffer (50 mM, pH 7.4, 0.85% sodium chloride). At forty minutes, over half of BSA turn into aggregate in solutions without excipient, while no significant change of BSA in the solution with excipient. The sample with excipient was further analyzed at incubation time of 60 minutes, and the aggregates started to show up in an insignificant amount. SEC column: TSK gel G3000 SW, 7.5.times.300 mm, Tosoh Biosciences, part number 05789. Mobile phase: 50 mM phosphate buffer, pH 7.4, 0.85% sodium chloride. Flow rate: 1.0 ml/min. Detection: 280 nm Instrument: BuckChrom BLC-20.

Example 2

Reduction of Aggregation of BSA Induced by Methanol

BSA stock solution (0.050 ml, 35%, 0.85% sodium chloride, Sigma) was diluted with 0.050 ml of sodium phosphate buffer (50 mM, pH 7.4, no sodium chloride) and 0.050 ml of water (HPLC grade). A separate sample was prepared in the same way, but replacing the 0.050 ml of water using 0.050 ml of an excipient solution containing pyridoxal phosphate (represented as X2 in FIG. 1, 100 mg/ml in water, pH 7.4). To each of the two samples in test tubes were added 0.350 ml of an aqueous solution of polyethylene glycol (molecular weight 3400, 75%) to turn the mixtures cloudy, followed by addition of 0.50 ml of methanol (HPLC grade). Then the samples were centrifuged to collect the precipitates. The precipitates were re-dissolved in PBS buffer and analyzed on Size Exclusion Chromatography HPLC. Without excipient, about two thirds of BSA was found in the form of aggregates, while only a quarter of BSA appeared as aggregate in the samples using excipient pyridoxal phosphate.

Example 3

Reduction of Aggregation of BSA Induced by t-Butanol

To three separate test tubes containing 0.050 ml of BSA (35%, 0.85% sodium chloride) and 0.050 ml of phosphate buffer (50 mM, pH 7.4), were respectively added 0.010 ml of water, 0.010 mll of 2-formylbenzenesulfonic acid sodium salt (75 mg/ml, pH 8), and 0.010 ml of pyridoxal phosphate (100 mg/ml, pH 7.4). To each of the three tubes were then added 0.50 ml of PEG solution (75%, molecular weight 3400) followed by centrifugation to give some precipitate. The three supernatants were collected to have BSA at saturated concentrations, and to them were separately added 0.50 ml of t-butanol to have more BSA precipitates after centrifugation. The crops of precipitates from t-butanol were washed with t-butanol twice (0.75 ml each) and re-dissolved in PBS buffer (50 mM sodium phosphate, pH 7.4, 0.85% sodium chloride) for SEC HPLC analysis. Plain BSA produced about 75% of aggregates, the sample with 2-formylbenzenesulfonic acid produced about 60% of aggregates, the sample with pyridoxal phosphate produced less than 50% of aggregates.

Example 4

Inhibition of BSA Thermal Aggregation by 4-formyl-1,3-benzenedisulfonic acid at 65° C. Over 60 min Using commercial BSA solution (Sigma Aldrich, 350 mg/ml, 0.85% NaCl), and a stock solution of 5-formylbenzene-1,3-disulfonic acid (Sigma Aldrich, represented as X5 in FIG. 2 below, 400 mg/ml, pH 7.4) in sodium phosphate buffer (0.1 M, pH 7.4), a series of sample solutions of BSA was prepared with this excipient at various concentrations at a final volume of 0.5 ml in capped glass test tubes. All samples were inserted into wells of heating block that was preset at 65° C.

As seen in Table 1, 4-Formyl-1,3-benzenedisulfonic acid prevents BSA (262 mg/ml) from turning into gellified solid, even at a concentration as low as 12.5 mg/ml.

TABLE 1

Stabilizing Effects of 4-Formyl-1,3-benzenedisulfonic Acid on BSA

| Samples/Components | 1 | 2 | 3 | 4 |
|---|---|---|---|---|
| [BSA], mg/ml | 262.5 | 262.5 | 262.5 | 262.5 |
| [Phosphate], pH 7.4, mM | 25 | 25 | 25 | 25 |
| [Excipient], mg/ml | 0 | 50 | 25 | 12.5 |
| Results, 65° C., 60 minutes | Solid | Clear Solution | Clear Solution | Clear Solution |

Figure 2:
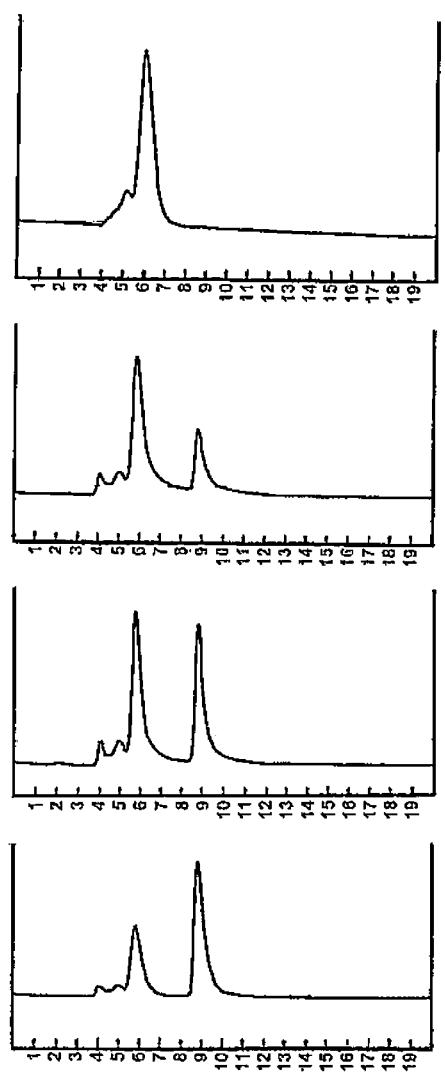
Figure 3:
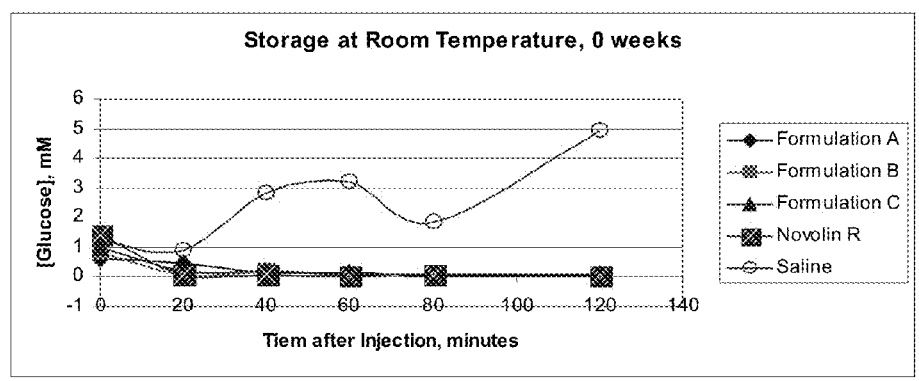
FIG. 3 is a graph of the Efficacy of Formulation A, B, C and Novolin R at The Start of Incubation at Room Temperature.
Figure 4:
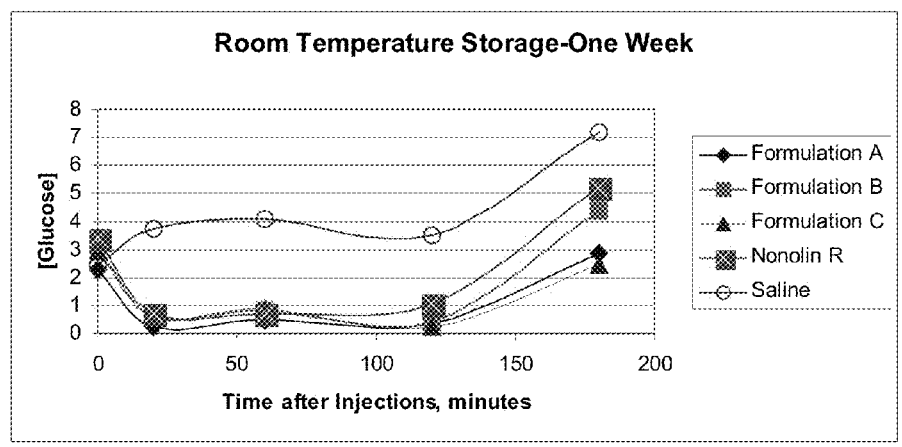
FIG. 4 is a graph of the Efficacy of Formulation A, B C and Novolin R at One Week of Incubation.
Figure 5:
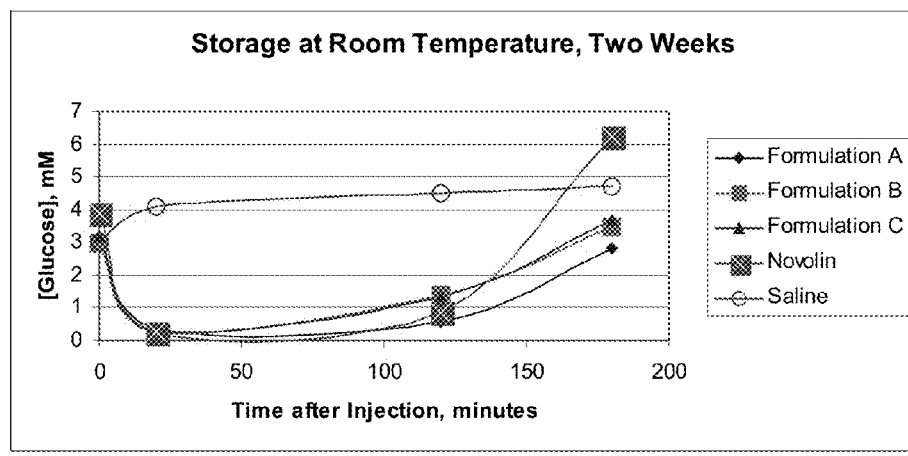
FIG. 5 is a graph of the Efficacy of Formulation A, B, C and Novolin R at Two Weeks of Incubation.
Figure 6:
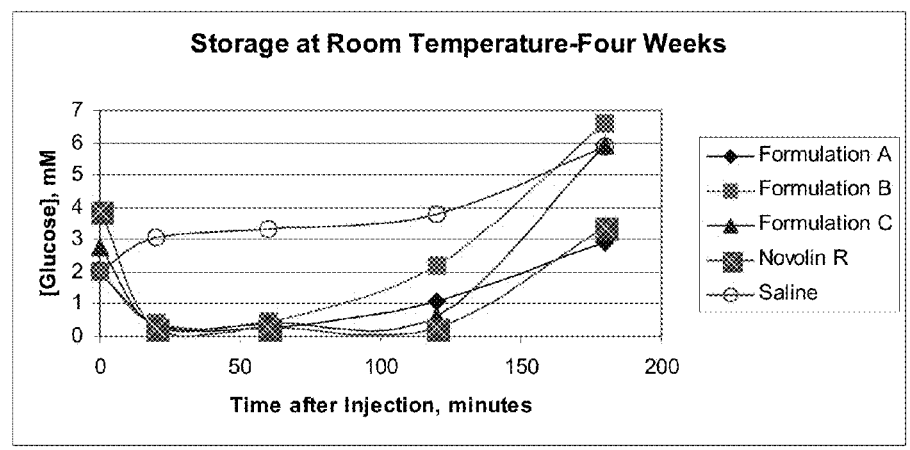
FIG. 6 is a graph of the Efficacy of Formulation A, B, C and Novolin R at Four Weeks of Incubation.
Figure 7:
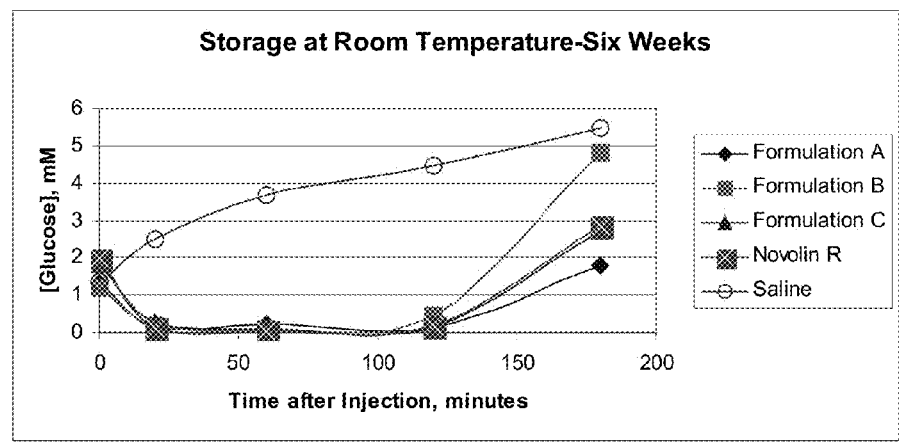
FIG. 7 is a graph of the Efficacy of Formulation A, B, C and Novolin R at Six Weeks of Incubation.

Ten microliter of the above clear solutions were each diluted with 1.0 ml of phosphate buffer (pH 7.4), and a reference sample of BSA solutions of 2.5 mg/ml was prepared in the same buffer. Small aliquot of 0.10 ml of all the five diluted samples were analyzed on SEC HPLC (TSK gel G 3000 SW, 5 mm.times.300 mm), eluted with 50 mM sodium phosphate buffer (pH 7.4) containing 0.85% sodium chloride at flow rate of 1.0 ml/min monitored at 280 nm. The HPLC chromatograms are illustrated in FIG. 2.

This was repeated at pH 6.8, and BSA solution with excipient (12.5 mg/ml) remained as clear solution, comparing to solidified BSA without excipient.

Example 5

Screening of Other Excipients at pH 6.2

Various excipients were tested for their capacity to deter BSA from forming a gel, using sucrose as a reference, in malonic acid buffer (25 mM), incubated at 65° C. for 60 minutes. The excipients used were sucrose, 4-formylbenzene-1,3-disulfonic acid, 4-formylbenzoic acid, phenylglyoxylic acid, glyoxylic acid. (Tables 2 through 6).

As can be seen in Table 2, sucrose does not have strong power to prevent BSA from turning into gel or solid.

TABLE 2

Effects of Excipient Sucrose

| Samples/Components | 1 | 2 | 3 | 4 |
|---|---|---|---|---|
| [BSA], mg/ml | 175 | 175 | 175 | 175 |
| [Malonate], pH 6.2, mM | 25 | 25 | 25 | 25 |
| [Excipient], mg/ml | 0 | 175 | 125 | 75 |
| Results, 65° C., 60 minutes | Solid | Gel | Pale Gel | Pale Gel |

TABLE 3

Effects of 4-Formylbenzene-1,3-disulfonic acid of Excipient

| Samples/Components | 1 | 2 | 3 | 4 |
|---|---|---|---|---|
| [BSA], mg/ml | 175 | 175 | 175 | 175 |
| [Malonate], pH 6.2, mM | 25 | 25 | 25 | 25 |
| [Excipient], mg/ml | 0 | 28.8 | 14.4 | 7.1 |
| Results, 65° C., 60 minutes | Solid | Clear Solution | Clear Solution | Clear Solution |

TABLE 4

Effects of 4-Formylbenzoic acid of Excipient

| Samples/Components | 1 | 2 | 3 | 4 |
|---|---|---|---|---|
| [BSA], mg/ml | 175 | 175 | 175 | 175 |
| [Malonate], pH 6.2, mM | 25 | 25 | 25 | 25 |
| [Excipient], mg/ml | 0 | 37.5 | 18.8 | 9.4 |
| Results, 65° C., 60 minutes | Solid | Clear Solution | Clear Solution | Clear Solution |

TABLE 5

Effects of Phenylglyoxylic Acid of Excipient

| Samples/Components | 1 | 2 | 3 | 4 |
|---|---|---|---|---|
| [BSA], mg/ml | 175 | 175 | 175 | 175 |
| [Malonate], pH 6.2, mM | 25 | 25 | 25 | 25 |
| [Excipient], mg/ml | 0 | 37.5 | 18.8 | 9.4 |
| Results, 65° C., 60 minutes | Solid | Clear Solution | Clear Solution | Clear Solution |

TABLE 6

Effects of Glyoxylic Acid of Excipient

| Samples/Components | 1 | 2 | 3 | 4 |
|---|---|---|---|---|
| [BSA], mg/ml | 175 | 175 | 175 | 175 |
| [Malonate], pH 6.2, mM | 25 | 25 | 25 | 25 |
| [Excipient], mg/ml | 0 | 23 | 11.5 | 5.8 |
| Results, 65° C., 60 minutes | Solid | Clear Solution | Clear Solution | Clear Solution |

As indicated in Table 3 through Table 6, each of the four excipients are effective in preventing BSA from turning into a gel or solid, even at very low concentrations.

Example 6

Inhibition of Myoglobin Thermal Aggregation at 65° C.

Myoglobin (Horse Skeleton, Sigma) was made into a stock solution (10 mg/ml) in sodium bicarbonate buffer (0.1 M, pH 9.0). This solution (0.5 ml) was then mixed with various excipient stock solutions (0.10 ml) to provide a series of test samples with the same final myoglobin concentration and varying excipient concentrations ([X]). Then the samples in sealed test tubes were inserted into wells of heating block that was pre-set at 65° C., and the incubation was continued over a period of time, to observe the formation of fibrillation precipitates (PPT). These results show that 4-Formylbenzene-1, 3-disulfonate was the best among this group to deter myoglobin from fibrillation.

TABLE 7

Excipient Effect on Myoglobin Thermal Aggregation at 65° C.

| [X], | 5-Formylbenzene-1,3-disulfonate | | | Benzeneglyoxylic Acid | | | Glyoxylic Acid | | | 3-Formyl-4-hydroxylbenzoic Acid | | | $H_2O$ |
|---|---|---|---|---|---|---|---|---|---|---|---|---|---|
| mM | 15 | 30 | 60 | 16.7 | 33.3 | 66.7 | 16.7 | 41.7 | 83.3 | 10 | 20 | 50 | — |
| 1 days | Clear | | | Precipitate (PPT) | | | PPT | | Clear | Precipitate | | | PPT |
| 2 days | Clear | | | Precipitate | | | PPT | | Clear | Precipitate | | | PPT |
| 4 days | Clear | | | Precipitate | | | Precipitate | | | Precipitate | | | PPT |
| 5 weeks | Clear | | | Precipitate | | | Precipitate | | | Precipitate | | | PPT |

Example 7

Inhibition of Insulin Fibrillation by Pyridoxal Phosphate at pH 7.4

A solution of zinc-free bovine insulin was prepared in phosphate buffer (50 mM, pH 7.4, no sodium chloride) at concentration of 1.2 mg/ml. Two aliquots of 2.0 ml each were transferred into two separate glass tubes (sanitized in boiling water), and 0.10 ml of water was added to one tube, and 0.10 ml of pyridoxal phosphate (100 mg/ml, in water, pH 7.4) was added to the other. Both tubes were capped and put on a rotator (12 rotations per minute) in an oven at temperature of 39° C. The tube of insulin without pyridoxal phosphate turned cloudy after three hours, while the one with pyridoxal phosphate still remained clear after five weeks.

Example 8

Inhibition of Insulin Fibrillation by Pyridoxal Phosphate at pH 7.0

A solution of zinc-free bovine insulin was prepared in phosphate buffer (50 mM, pH 7.0, no sodium chloride) at concentration of 1.2 mg/ml. Two aliquots of 2.0 ml each were transferred into two separate glass tubes (sanitized in boiling water), and 0.10 ml of water was added to each tube. To 4.0 ml of the insulin solution was added 0.20 ml of pyridoxal phosphate (100 mg/ml, in water, pH 7.4) and the pH was adjusted to 7.0, and divided into two separate glass tubes (sanitized in boiling water). All the four tubes were capped and put on a rotator (12 rotations per minute) in an oven at temperature of 39° C. The two tubes of insulin without pyridoxal phosphate turned cloudy after five hours, while the other two with pyridoxal phosphate still remained clear beyond four weeks.

Example 9

Inhibition of Insulin Fibrillation by Pyridoxal Phosphate of Varied Concentrations at pH 7.4

A solution of zinc-free bovine insulin (50 mg) was dissolved in 0.50 ml of 0.1 N hydrochloric acid, and neutralized using 0.1 N sodium hydroxide until it turned cloudy and clear again. Then 0.667 ml of pyridoxal phosphate solution (167 mg/ml, pH 7.0 in water) was added to the insulin solution, and the pH was re-adjusted to 7.4 using dilute sodium hydroxide. The total volume was adjusted to 2.5 ml with HPLC grade water. Serial dilution using water provided four samples (1.0 ml each) of insulin concentrations at 2.0, 5.0, 10, 15 mg/ml. All the four samples in glass vials, together with 0.5 ml of the remaining insulin-pyridoxal phosphate solution (20 mg/ml) were capped and put on a rotator (12 rotations per minute) in an oven at temperature of 39° C. All samples still remained clear after three weeks.

Example 10

Animal Study of Three New Formulations of Zinc-Free Recombinant Human Insulin with New Excipients A solid sample of zinc-free recombinant human insulin (27 mg) was dissolved in 1.0 ml of HPLC grade water containing 0.10 ml of hydrochloric acid (0.10 N). To this solution was added 2.4 ml of sodium phosphate buffer (0.10 M, pH 7.0), followed by 3 drops of sodium hydroxide (0.05 N) to give a clear solution. This solution was diluted with water to 9.0 ml, and divided equally into three portions. Portion A (3.0) was mixed with 0.166 ml of 5-formylbenzene-1,3-disulfonic acid (pH 6.7, 360 mM) to give a final pH of 6.9, followed by further dilution with water to 6.0 ml. Portion B (3.0 ml) was mixed with 0.60 ml of glyoxylic acid (pH 7.0, 100 mM) to give a final pH of 6.9, followed by further dilution with water to 6.0 ml. Portion C (3.0 ml) was mixed with 0.60 ml of 3-formyl-4-hydroxybenzoic acid (pH 6.8, 100 mM) and a few drops of NaOH (0.05 N) to give a final pH of 6.9, followed by further dilution with water to 6.0 ml. All three solutions (formulation A, B, C) were filtered through 0.2 microns filter, and stored at room temperature for animal study using Novolin (stored at 2-8° C. throughout the entire experiment) and saline as references.

Each of the three formulations (A, B, C) and Novolin R was diluted with saline to 0.91 IU/ml, and the dose was calculated at the rate of 9.1 IU/Kg. Each formulation was injected to a group of 8 mice subcutaneously on their back. Blood samples were taken right before injection, and at various time points after injection. The glucose concentrations (mM) were determined by standard Monroe method.

TABLE 8

Blood Sugar Lowering Effects of Samples at the Start of Incubation

| | Time, Minutes | | | | | |
|---|---|---|---|---|---|---|
| | 0 min | 20 min | 40 min | 60 min | 80 min | 120 min |
| A | 0.64 | 0.46 | 0.11 | 0.11 | 0.01 | 0.01 |
| B | 0.84 | 0.08 | 0.16 | 0.04 | 0.07 | 0.04 |
| C | 1.00 | 0.19 | 0.16 | 0.08 | 0.07 | 0.07 |
| Novolin R | 1.04 | 0.05 | 0.07 | 0.01 | 0.05 | 0.03 |
| Saline | 1.22 | 0.91 | 2.80 | 3.19 | 1.84 | 4.93 |

TABLE 9

Blood Sugar Lowering Effects of Samples at One Week Incubation

| | Time, Minutes | | | | |
|---|---|---|---|---|---|
| | 0 | 20 | 60 | 120 | 180 |
| A | 2.28 | 0.26 | 0.49 | 0.35 | 2.84 |
| B | 3.08 | 0.56 | 0.80 | 0.39 | 4.39 |
| C | 2.92 | 0.57 | 0.88 | 0.21 | 2.44 |
| Novolin R | 3.38 | 0.71 | 0.68 | 1.04 | 5.22 |
| Saline | 2.45 | 3.75 | 4.10 | 3.50 | 7.17 |

TABLE 10

Blood Sugar Lowering Effects of Samples at Two Weeks Incubation

| | Time (minutes) | | | |
|---|---|---|---|---|
| | 0 | 20 | 120 | 180 |
| A | 3.16 | 0.34 | 0.58 | 2.82 |
| B | 2.97 | 0.27 | 1.37 | 3.50 |
| C | 3.17 | 0.29 | 1.31 | 3.70 |
| Novolin R | 3.89 | 0.28 | 0.88 | 6.21 |
| Saline | 3.02 | 4.10 | 4.51 | 4.71 |

TABLE 11

Hyperglycemic Effects of Samples at Four Weeks Incubation

| | Time (minutes) | | | | |
|---|---|---|---|---|---|
| | 0 | 20 | 60 | 120 | 180 |
| A | 3.23 | 0.36 | 0.26 | 1.09 | 2.91 |
| B | 1.98 | 0.41 | 0.45 | 2.21 | 6.57 |
| C | 2.74 | 0.33 | 0.42 | 0.62 | 5.93 |
| Novolin R | 3.89 | 0.24 | 0.23 | 0.25 | 3.38 |
| N.S | 2.04 | 3.09 | 3.30 | 3.80 | 5.90 |

TABLE 12

Hyperglycemic Effects of Samples at Six Weeks Incubation

| | Time (minutes) | | | | |
|---|---|---|---|---|---|
| | 0 | 20 | 60 | 120 | 180 |
| A | 1.30 | 0.14 | 0.20 | 0.15 | 1.81 |
| B | 1.20 | 0.19 | 0.10 | 0.43 | 4.81 |
| C | 1.85 | 0.28 | 0.07 | 0.13 | 2.71 |
| Novolin R | 1.93 | 0.13 | 0.05 | 0.19 | 2.85 |
| N.S | 1.37 | 2.48 | 3.70 | 4.48 | 5.48 |

Example 11

Inhibition of Insulin Fibrillation by Glyoxylic Acid

A solution of zinc-free recombinant human insulin was prepared in phosphate buffer (50 mM, pH 7.0, no sodium chloride) at concentration of 1.0 mg/ml, containing 0 and 20 mM glyoxylic acid. Commercial NovoRapid (Novo Nordisk, 100 IU/ml) was diluted with phosphate buffer to 25 IU/ml, with and without glyoxylic acid (0 or 20 mM). Humalog 25 (100 IU/ml, Eli Lilly) was centrifuged to collect the supernatant, and the LisPro concentration was assumed to be 25 IU/ml. Then two LisPro samples were made with and without glyoxylic acid (0 or 20 mM) with assumed final LisPro concentration of 20 IU/ml. Each of the samples (1.0 ml) was transferred into a capped 10 ml test tube, and loaded onto a rotator that was set at 12 rotations per minute at room temperature. All insulins without glyoxylic acid turned cloudy within two days, while the samples with glyoxylic acid stayed in clear solutions beyond four weeks.

Example 12

Inhibition of Zinc Insulin Fibrillation by Glyoxylic Acid

Conditions were as in Example 11 above, but using commercial Humulin R (100 IU/ml). On the rotator, Humulin R without glyoxylic acid yielded a precipitate within two days, while the one containing glyoxylic acid remained clear six days before turning cloudy.

The invention claimed is:

1. A method of minimizing or preventing protein aggregation comprising reacting a compound bearing (1) one or more carbonyl groups and (2) a charge or a bulky group with a protein and forming a reversible Schiff bond with an amino group of the protein surface, where the compound is selected from the group consisting of:

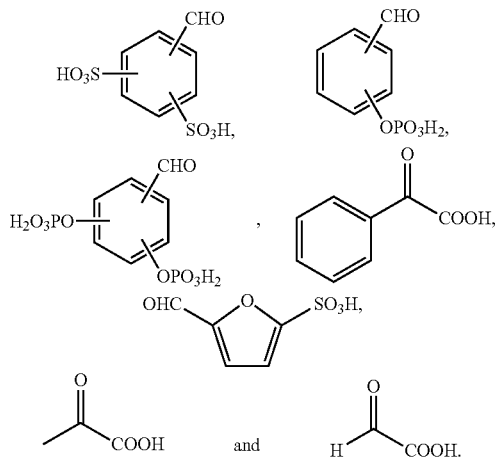

2. A method of minimizing or preventing protein aggregation comprising reacting a compound bearing (1) one or more carbonyl groups and (2) a charge or a bulky group with a protein and forming a reversible Schiff bond with an amino group of the protein surface, where the compound is 2-formylbenzenesulfonic acid.

3. The method of claim 1, where the compound 4-formyl-1,3-benzenedisulfonic acid.

4. A method of minimizing or preventing protein aggregation comprising reacting a compound bearing (1) one or more carbonyl groups and (2) a charge or a bulky group with a protein and forming a reversible Schiff bond with an amino group of the protein surface, where the compound is 4-formylbenzoic acid.

5. The method of claim 1, where the compound is phenylglyoxylic acid.

6. The method of claim 1, where the compound is glyoxylic acid.

\* \* \* \* \*